(12) United States Patent
Eckhardt et al.

(10) Patent No.: US 8,142,477 B2
(45) Date of Patent: Mar. 27, 2012

(54) RETAINING SYSTEM

(75) Inventors: Jason John Eckhardt, Memphis, TN (US); Vincent C. Traynelis, Chicago, IL (US); J. Kenneth Burkus, Columbus, GA (US); Regis W. Haid, Jr., Atlanta, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 178 days.

(21) Appl. No.: 12/691,461

(22) Filed: Jan. 21, 2010

(65) Prior Publication Data

US 2011/0178551 A1 Jul. 21, 2011

(51) Int. Cl.
*A61B 17/70* (2006.01)

(52) U.S. Cl. .............. 606/246; 623/17.11; 623/17.16

(58) Field of Classification Search .......... 606/246–249; 623/17.11–17.16
See application file for complete search history.

(56) References Cited

U.S. PATENT DOCUMENTS

| | | | |
|---|---|---|---|
| 3,221,793 A | 12/1965 | Gutshall |
| 3,438,300 A | 4/1969 | Blom et al. |
| 3,541,798 A | 11/1970 | Schnabel, Jr. |
| 4,988,351 A | 1/1991 | Paulos et al. |
| 5,256,020 A | 10/1993 | Ikeda et al. |
| 5,312,404 A | 5/1994 | Asher et al. |
| 5,906,466 A | 5/1999 | Eandi |
| 5,984,924 A | 11/1999 | Asher et al. |
| 6,001,130 A | 12/1999 | Bryan et al. |
| 6,355,038 B1 | 3/2002 | Pisharodi |
| 6,514,257 B2 | 2/2003 | Dovesi et al. |
| 6,517,579 B1 | 2/2003 | Paulos et al. |
| 6,524,316 B1 | 2/2003 | Nicholson et al. |
| 6,530,933 B1 | 3/2003 | Yeung et al. |
| 6,669,697 B1 | 12/2003 | Pisharodi |
| 6,689,133 B2 | 2/2004 | Morrison et al. |
| 6,918,934 B2 | 7/2005 | Ralph et al. |
| 7,001,389 B1 | 2/2006 | Navarro et al. |
| 7,314,486 B2 | 1/2008 | Ralph et al. |
| 7,588,590 B2 | 9/2009 | Chervitz et al. |
| 7,604,659 B2 | 10/2009 | Lee |
| 2003/0105524 A1 | 6/2003 | Paulos et al. |
| 2004/0097927 A1 | 5/2004 | Yeung et al. |
| 2004/0106925 A1 | 6/2004 | Culbert |
| 2004/0127906 A1 | 7/2004 | Culbert et al. |
| 2005/0033433 A1 | 2/2005 | Michelson |
| 2006/0189991 A1 | 8/2006 | Bickley |
| 2006/0276897 A1 | 12/2006 | Winslow et al. |
| 2007/0123863 A1 | 5/2007 | Winslow et al. |
| 2008/0255622 A1 | 10/2008 | Mickiewicz et al. |
| 2009/0210062 A1* | 8/2009 | Thalgott et al. ............ 623/17.16 |

* cited by examiner

*Primary Examiner* — Eduardo C Robert
*Assistant Examiner* — Christina Negrelli

(57) ABSTRACT

A retaining system for affixing a component to a vertebral body is disclosed. The system comprises a component and a retaining mechanism. The component comprises an inner surface configured to engage at least a portion of an endplate surface of the vertebral body, and an outer surface configured to engage the retaining mechanism, wherein the outer surface of the component comprises a first face directed substantially toward the vertebral body. The retaining mechanism comprises an inner surface configured to engage the outer surface of the component, and an outer surface configured to receive a fastener, wherein the inner surface of the retaining mechanism comprising a second face directed substantially away from the vertebral body.

20 Claims, 10 Drawing Sheets

RETAINING SYSTEM

FIELD OF INVENTION

The present invention is directed to systems or mechanisms for affixing a prosthesis or portion of a prosthesis to bone.

BACKGROUND

The present disclosure relates to mechanisms for affixing prostheses to bone, and more particularly, systems for affixing at least a portion of a prosthesis to bone.

SUMMARY OF THE INVENTION

A retaining system for affixing a component to a vertebral body is disclosed. The system comprises a component and a retaining mechanism. The component comprises an inner surface configured to engage at least a portion of an endplate surface of the vertebral body, and an outer surface configured to engage the retaining mechanism, wherein the outer surface of the component comprises a first face directed substantially toward the vertebral body. The retaining mechanism comprises an inner surface configured to engage the outer surface of the component, and an outer surface configured to receive a fastener, wherein the inner surface of the retaining mechanism comprising a second face directed substantially away from the vertebral body.

Additional aspects and features of the present disclosure will be apparent from the detailed description and claims as set forth below.

DETAILED DESCRIPTION

Figure 1:
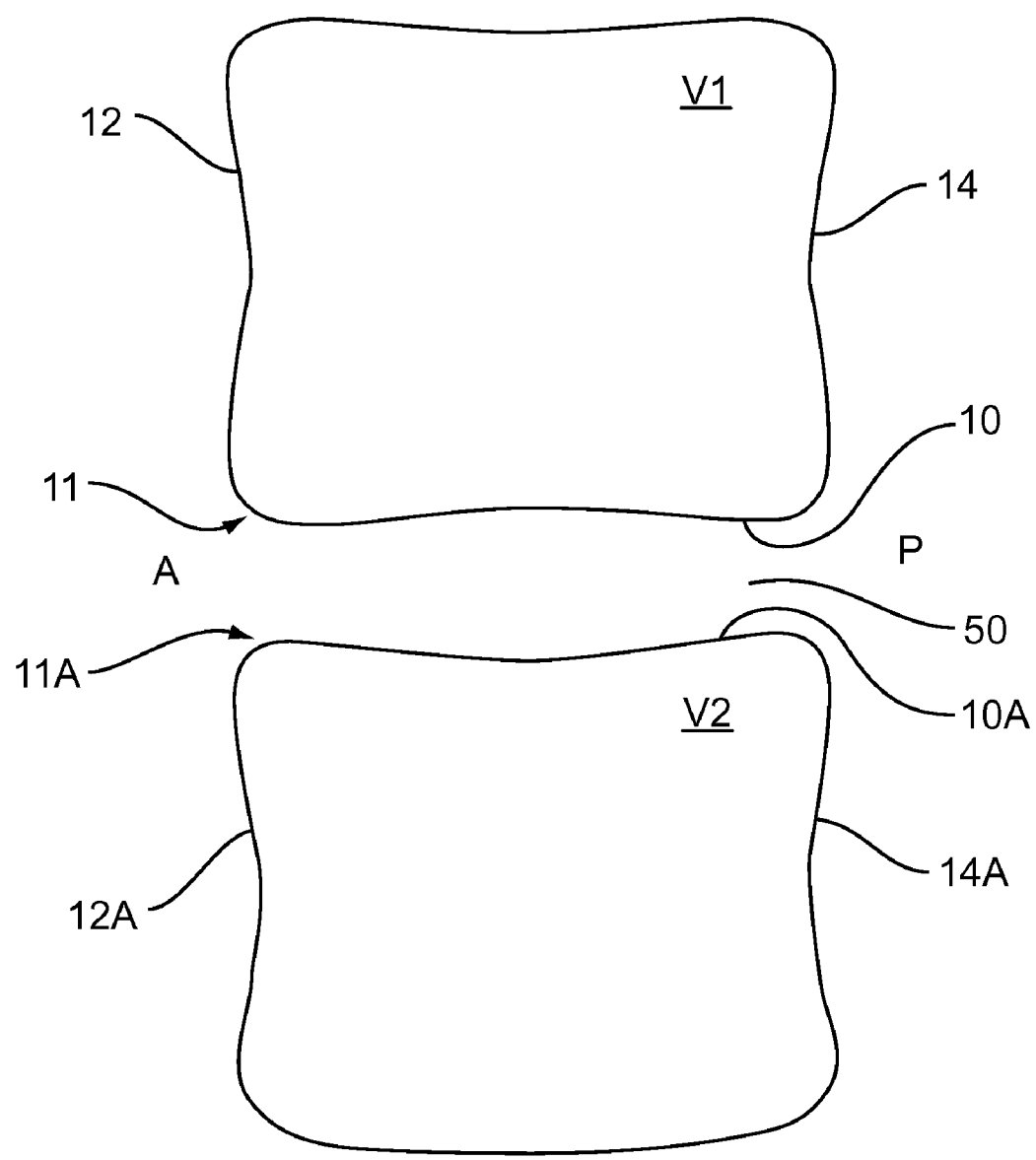
FIG. 1 is a schematic, cross-sectional view of two adjacent vertebral bodies after a disc situated between the two is removed.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a schematic, cross-sectional view of two adjacent vertebral bodies V1 and V2 after a disc situated between the two is removed. FIG. 1 depicts a superior vertebral body V1, an inferior vertebral body V2, and a disc space 50 between the two vertebral bodies V1 and V2. Reference marker A represents an anterior side of the vertebral bodies V1 and V2, whereas reference marker P represents a posterior side of the vertebral bodies V1 and V2. As shown in FIG. 1, superior vertebral body V1 has an anterior vertical surface 12, a posterior vertical surface 14, an endplate surface 10, and a junction 11 between the vertical surface 12 and the endplate surface 10. Similarly, as shown in FIG. 1, inferior vertebral body V2 has an anterior vertical surface 12A, a posterior vertical surface 14A, an endplate surface 10A, and a junction 11A between the vertical surface 12A and the endplate surface 10A. FIG. 1 shows a schematic, cross-sectional view of an anatomical shape of the vertebral body V1.

Figure 2:
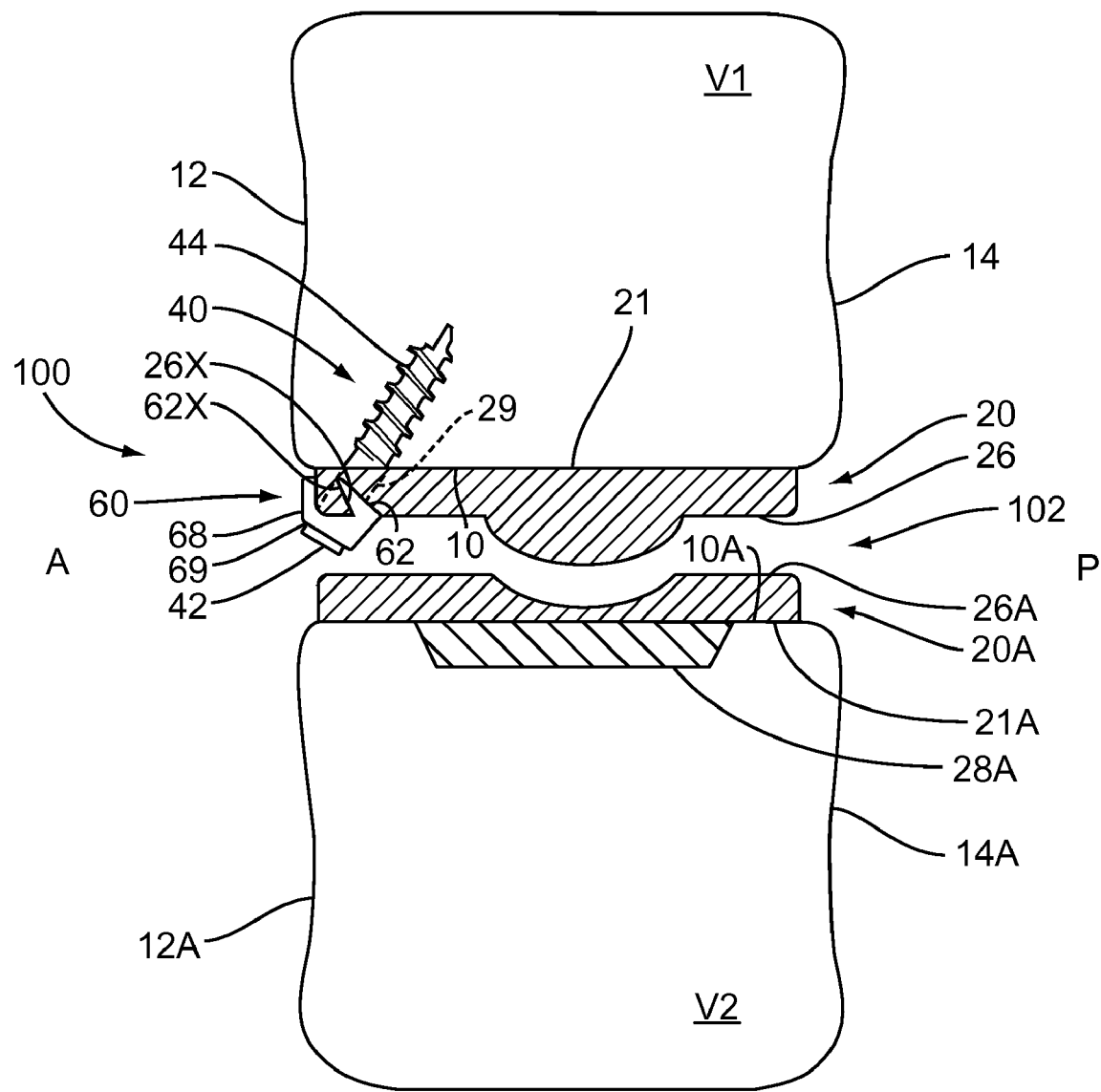
FIG. 2 is a schematic, cross-sectional view of a retaining system in a sagittal plane.

FIG. 2 shows a schematic, cross-sectional view of a retaining system 100 in a sagittal plane, situated substantially in the disc space 50 between vertebral bodies V1 and V2. Reference marker A represents an anterior side of the vertebral bodies V1 and V2, whereas reference marker P represents a posterior side of the vertebral bodies V1 and V2. The system 100 is a retaining system for affixing a component to a vertebral body. As shown in FIG. 2, the system 100 comprises a component 20 and a retaining mechanism 60. Component 20 comprises an inner surface 21 configured to engage at least a portion of an endplate surface 10 of the vertebral body V1, and an outer surface 26 configured to engage the retaining mechanism 60. The outer surface 26 of the component 20 comprises a first face 26X directed substantially toward the vertebral body V1. The retaining mechanism 60 comprises an inner surface 62 configured to engage the outer surface 26 of the component 20, and an outer surface 68 configured to receive a fastener 40. The inner surface 62 of the retaining mechanism 60 comprises a second face 62X directed substantially away from the vertebral body V1. Note that although FIG. 2 shows component 20 configured to engage at least a portion of endplate surface 10 of the vertebral body V1, component 20 may be configured to engage any portion of vertebral body V1, or any portion of any bone.

The term "substantially" (or "substantial") as used herein may be applied to modify any quantitative representation which could permissibly vary without resulting in a change in the basic function to which it is related. For example, while the first face 26X of the outer surface 26 of component 20 is directed substantially toward the vertebral body V1, it is directed more toward the vertebral body V1 than away from it. Similarly, the second face 62X of the inner surface 62 of the retaining mechanism 60 is directed more away from the vertebral body than toward it. As shown in FIG. 2, the first face 26X and the second face 62X oppose each other. Also as shown, the first face 26X and the second face 62X engage each other, and because they face opposite directions, the first face 26X respectively prevent the retaining mechanism 60 from moving toward the anterior side A of the vertebral body V1, and the second face 62X prevents the component 20 from moving toward the posterior side P of the vertebral body V2.

Further, as shown in FIG. 2, fastener 40 passes through the retaining mechanism and through component 20 so that the fastener 40 can engage the vertebral body V1, as shown. In FIG. 2, the prosthesis 102 is a motion-preserving device and that component 20A does not utilize a retaining mechanism or fastener to affix the component 20A to vertebral body V2, but rather utilizes a structure 28A. Structure 28A may be anchors, keels, spikes, pegs, prongs, or similar structures to help component 20A affix to vertebral body V2. Surface coatings such as Hydroxyapatite (HA), plasma spray or beading also may be used instead of or in addition to respective structure 28A to help affix components to their respective vertebral bodies. Component 20A may, however, utilize a retaining mechanism and fastener similar to those used in conjunction with component 20. Similarly, in helping affix component 20 to vertebral body V1, component 20 may utilize a structure similar to structure 28A and/or surface coatings in addition to the retaining mechanism 60 and fastener 40.

Fastener 40 has a distal end 44 and a fastener head 42. As shown, fastener 40 is a screw. As shown in FIG. 2, the retaining system 100 is configured so that the fastener 40 can penetrate the vertebral body V1, and more particularly, the system 100 is configured so that the fastener 40 is received from an anterior direction. Further, as shown in FIG. 2, the retaining mechanism 60 further comprises a fastener-receiving hole 69 configured to receive the fastener 40 and to allow the fastener 40 to engage the vertebral body V1. Also, as shown in FIG. 2, the component 20 further comprises a fastener-receiving hole 29 configured to receive the fastener 40 and to allow the fastener 40 to engage the vertebral body V1. Further, as shown in FIG. 2, both fastener-receiving hole 29 and fastener-receiving hole 69 are configured to allow the fastener 40 to engage the vertebral body V1 in a direction toward a substantial center of the vertebral body V1.

Figure 2A:
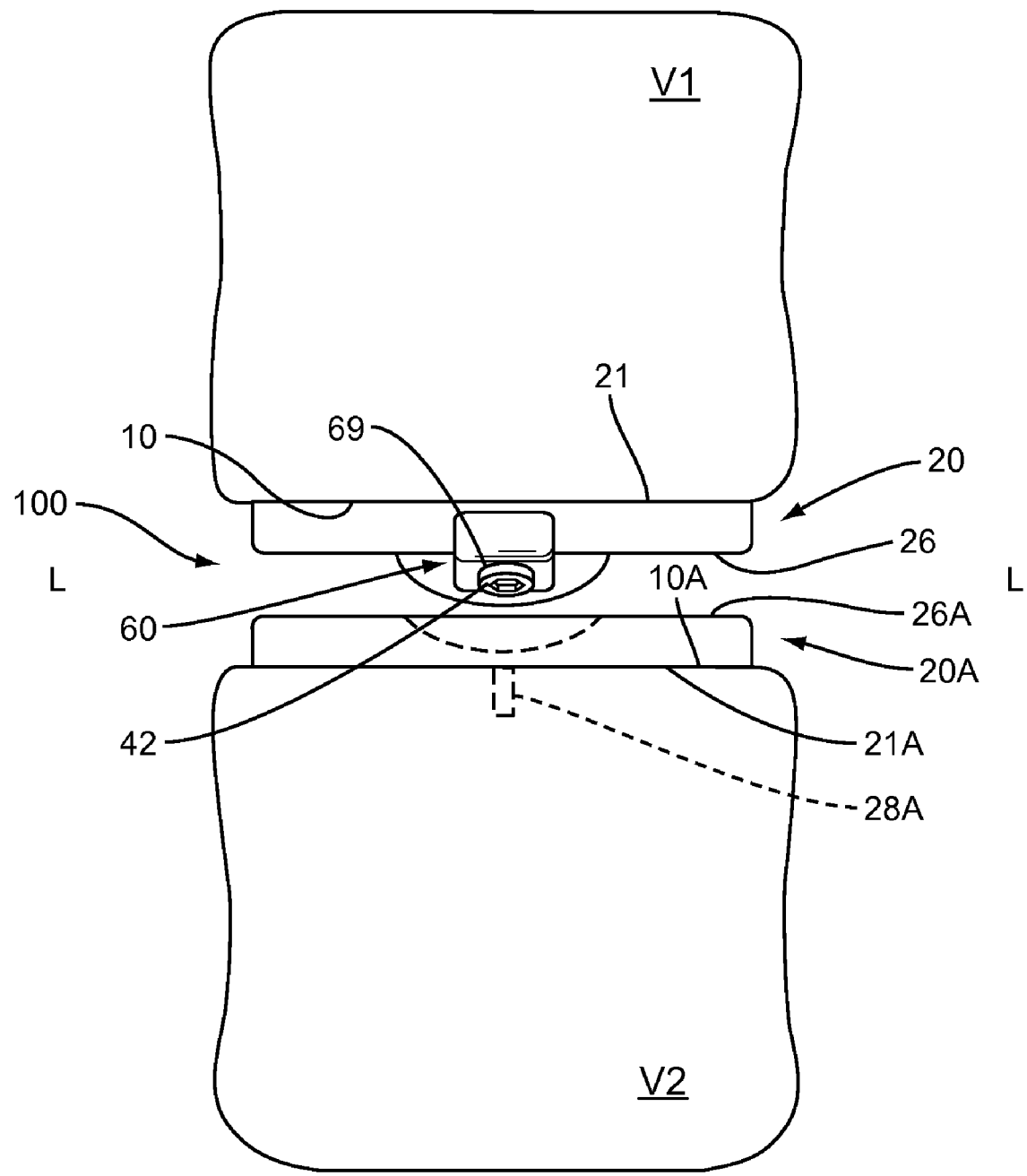
FIG. 2A is a frontal view the retaining system of FIG. 2, i.e., a view from the anterior side of vertebral bodies V1 and V2.

FIG. 2A shows a frontal view of retaining system 100 of FIG. 2. This view is from the anterior side A of vertebral bodies V1 and V2, where reference marker L represents lateral sides of vertebral bodies V1 and V2. As shown in FIG. 2A, retaining system 100 comprises a single retaining mechanism 60 and a single fastener 40 (of which fastener head 42 is visible). Further, FIG. 2A shows the fastener-receiving hole 69 of retaining mechanism 60, the hole 69 of which is configured to receive fastener 40 and to allow fastener 40 to engage the vertebral body V1.

Figure 2B:
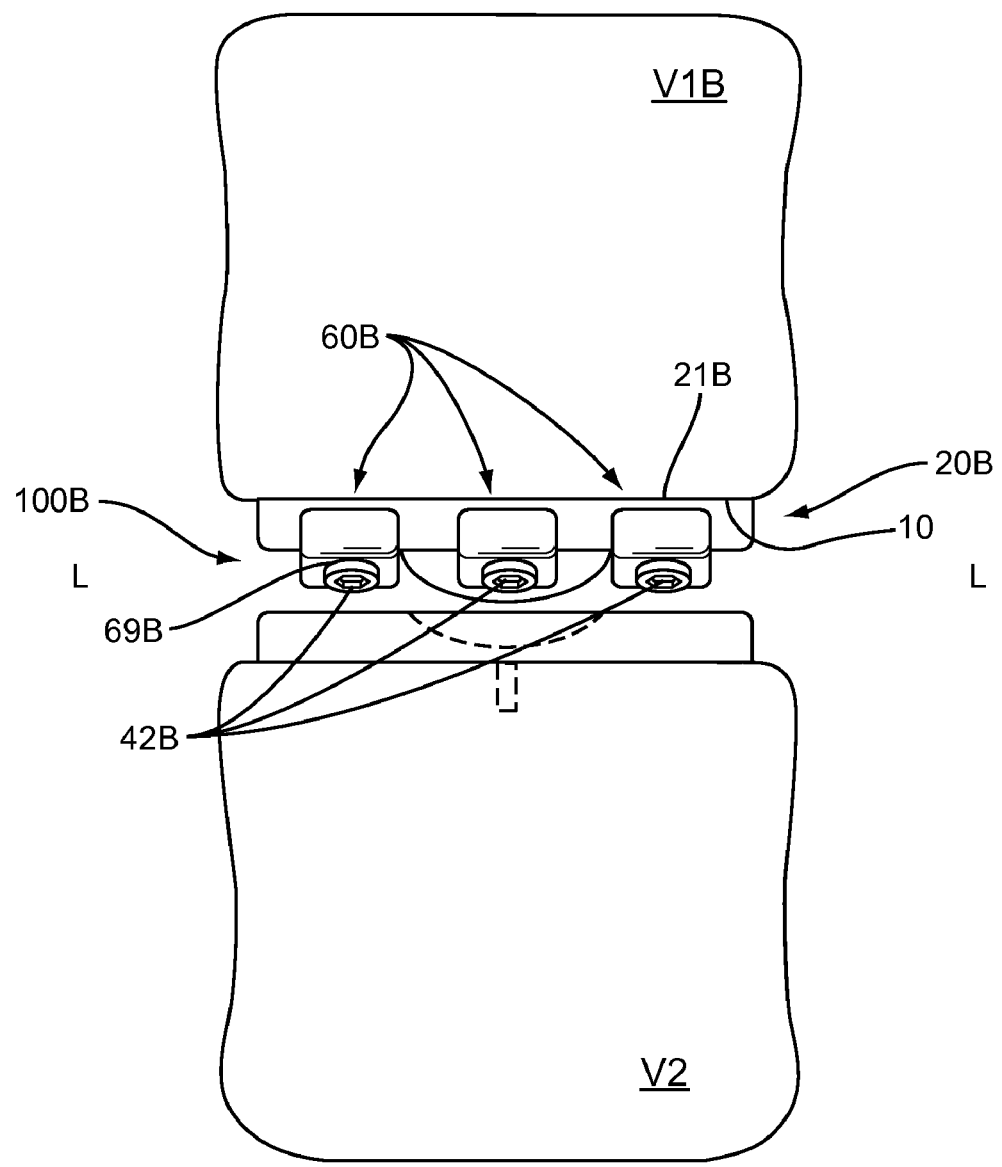
FIG. 2B is a frontal view of an alternate retaining system.

FIG. 2B shows a frontal view of an alternate retaining system 100B of FIG. 2. This view is from the anterior side A of vertebral bodies V1B and V2B, where reference marker L represents lateral sides of vertebral bodies V1B and V2B. As shown in FIG. 2B, retaining system 100B comprises three retaining mechanisms 60B, each of which are situated at different areas along the endplate surface 10 near junction 11. Each retaining mechanism 60B provides an area for helping component 20B affix to vertebral body V1B. Further, as shown, each retaining mechanism 60B comprises a fastener-receiving hole 69B for receiving a fastener 40B and for allowing each fastener 40B to engage the vertebral body V1. As shown in the frontal view of FIG. 2B, fastener heads 42B are visible.

Figure 2C:
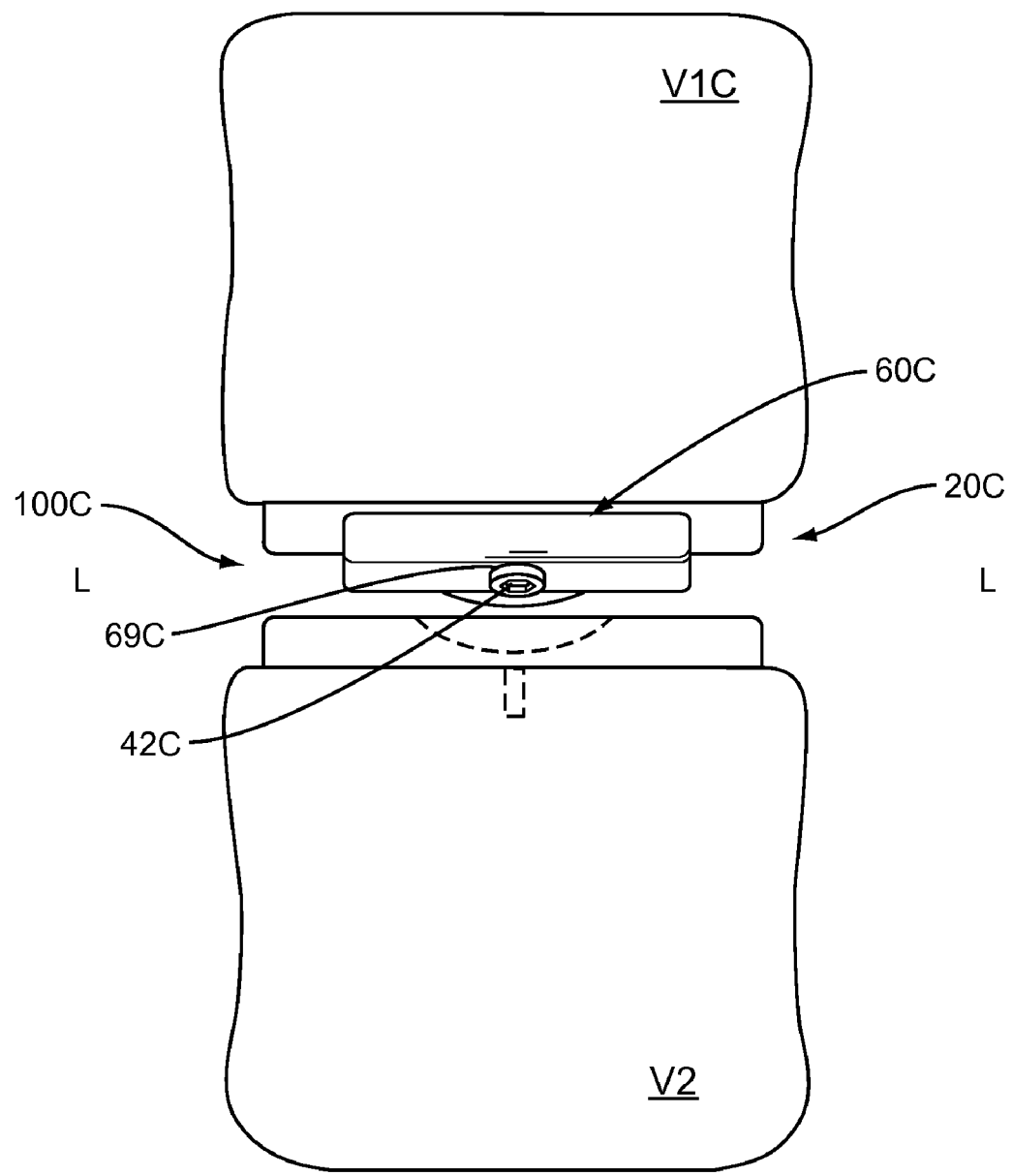
FIG. 2C is a frontal view of an alternate retaining system.

FIG. 2C shows a frontal view of an alternate retaining system 100C of FIG. 2. This view is from the anterior side A of vertebral bodies V1B and V2B, where reference marker L represents lateral sides of vertebral bodies V1B and V2B. As shown in FIG. 2C, retaining system 100C comprises a single retaining mechanism 60C, but as opposed to retaining mechanism 60, retaining mechanism 60C extends over a larger portion of endplate surface 10. As shown, the width (in the L-L direction) of retaining mechanism is at least half of the width of component 20C. The retaining mechanism 60C provides an area for helping component 20C affix to vertebral body V1C. Further, as shown, the retaining mechanism 60C comprises a fastener-receiving hole 69C for receiving a fastener and for allowing the fastener to engage the vertebral body V1. As shown in the frontal view of FIG. 2C, fastener head 42C is visible. Although a single fastener-receiving hole 69C and single fastener are used in system 100C, multiple fastener-receiving holes and fasteners may be utilized.

Figure 3:
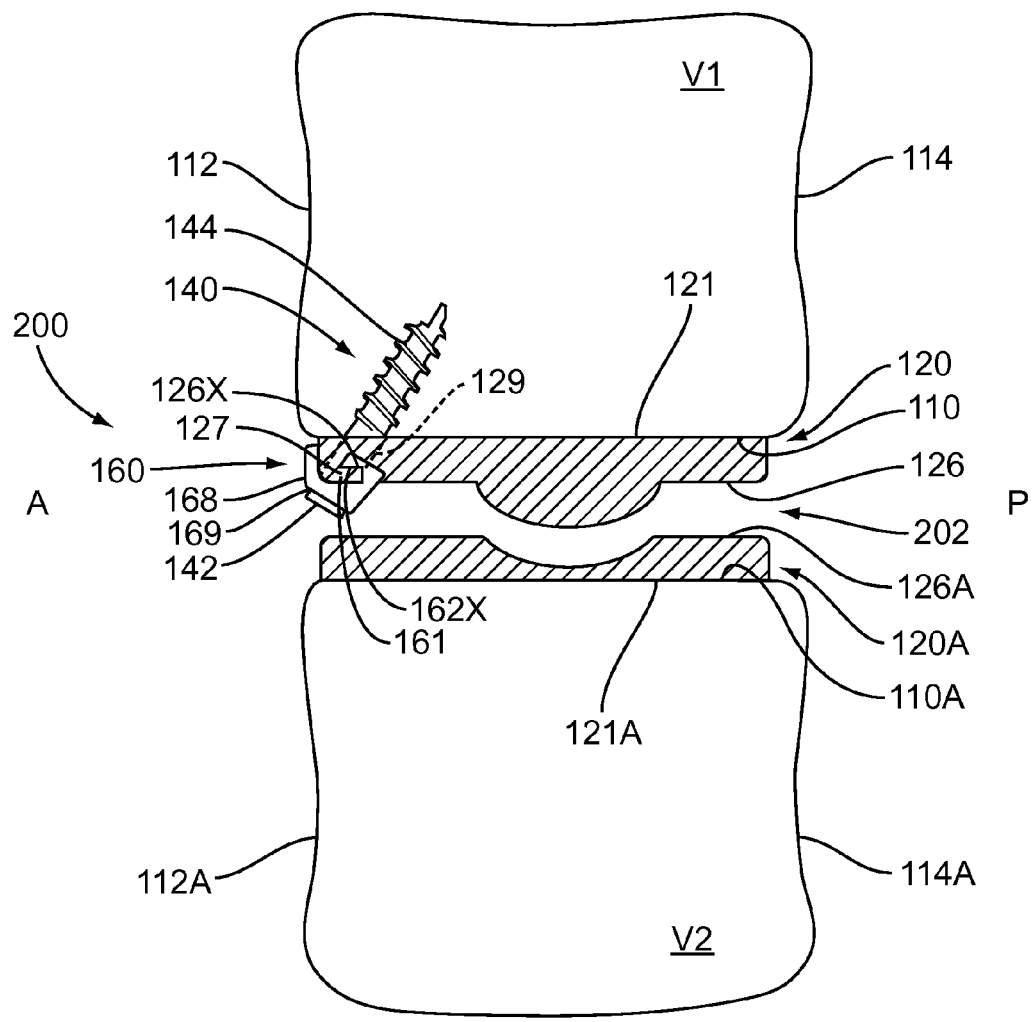
FIG. 3 is a schematic, cross-sectional view of another retaining system in a sagittal plane.

FIG. 3 shows a schematic, cross-sectional view of a retaining system 200 in a sagittal plane, situated substantially in the disc space 50 between vertebral bodies V1 and V2. Reference marker A represents an anterior side of the vertebral bodies V1 and V2, whereas reference marker P represents a posterior side of the vertebral bodies V1 and V2. The system 200 is a retaining system for affixing a component to a vertebral body. As shown in FIG. 3, the system 200 comprises a component 120 and a retaining mechanism 160. Component 120 comprises an inner surface 121 configured to engage at least a portion of an endplate surface 110 of the vertebral body V1, and an outer surface 126 configured to engage the retaining mechanism 160. The outer surface 126 of the component 120 comprises a first face 126X directed substantially toward the vertebral body V1. The retaining mechanism 160 comprises an inner surface 162 configured to engage the outer surface 126 of the component 120, and an outer surface 168 configured to receive a fastener 140. The inner surface 162 of the retaining mechanism 160 comprises a second face 162X directed substantially away from the vertebral body.

As shown in FIG. 3, the inner surface 162 of the retaining mechanism 160 further comprises a recessed area 161. Further, as shown in FIG. 3, inner surface 162 is not curved in the sagittal plane. Specifically, as shown in FIG. 3, the inner surface 162 does not have curves in the sagittal plane. Note, however, that the recessed area 161 and/or the inner surface 162 may have curves in the sagittal plane. Also, as shown in FIG. 3, the recessed area 161 is shaped to accommodate a projection 127 of component 120. Further, this relationship between the recessed area 161 of the retaining mechanism 160 and the projection 127 of the component 120 also is present in retaining system 100.

Further, as shown in FIG. 3, fastener 140 passes through the retaining mechanism and through component 120 so that the fastener 140 can engage the vertebral body V1, as shown. In FIG. 3, the prosthesis 202 is a motion-preserving device.

Fastener 140 has a distal end 144 and a fastener head 142. As shown, fastener 140 is a screw. As shown in FIG. 3, the retaining system 200 is configured so that the fastener 140 can penetrate the vertebral body V1, and more particularly, the system 200 is configured so that the fastener 140 is received from an anterior direction. Further, as shown in FIG. 2, the retaining mechanism 160 further comprises a fastener-receiving hole 169 configured to receive the fastener 140 and to allow the fastener 140 to engage the vertebral body V1. Also, as shown in FIG. 3, the component 120 further comprises a fastener-receiving hole 129 configured to receive the fastener 140 and to allow the fastener 140 to engage the vertebral body V1. Further, as shown in FIG. 2, both fastener-receiving hole 129 and fastener-receiving hole 169 are configured to allow the fastener 140 to engage the vertebral body V1 in a direction toward a substantial center of the vertebral body V1.

A frontal view of retaining system 200 of FIG. 3 may appear similar to any of the frontal views of FIGS. 2A, 2B and 2C.

Figure 4:
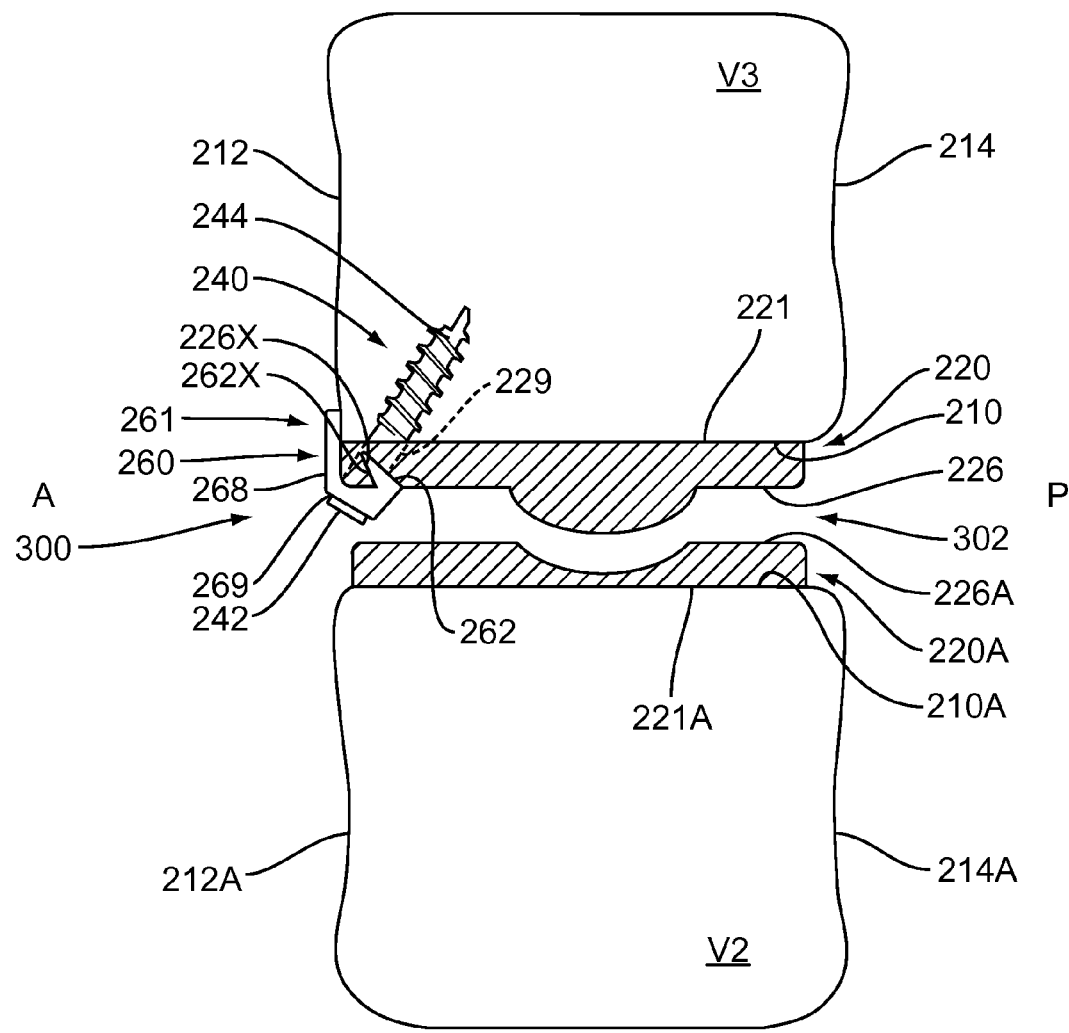
FIG. 4 is a schematic, cross-sectional view of another retaining system in a sagittal plane.

FIG. 4 shows a schematic, cross-sectional view of a retaining system 300 in a sagittal plane, situated substantially in the disc space 50 between vertebral bodies V3 and V2. Reference marker A represents an anterior side of the vertebral bodies V3 and V2, whereas reference marker P represents a posterior side of the vertebral bodies V3 and V2. The system 200 is a retaining system for affixing a component to a vertebral body. As shown in FIG. 4, the system 300 comprises a component 220 and a retaining mechanism 260. Component 220 comprises an inner surface 221 configured to engage at least a portion of an endplate surface 210 of the vertebral body V3, and an outer surface 226 configured to engage the retaining mechanism 260. The outer surface 226 of the component 220 comprises a first face 226X directed substantially toward the vertebral body V3. The retaining mechanism 260 comprises an inner surface 262 configured to engage the outer surface 226 of the component 220, and an outer surface 268 configured to receive a fastener 240. The inner surface 262 of the retaining mechanism 260 comprises a second face 262X directed substantially away from the vertebral body.

Further, as shown in FIG. 4, the retaining mechanism 260 is further configured to engage at least a portion of a vertical surface of the vertebral body. Specifically, the inner surface 262 of the retaining mechanism 260 is configured to engage a portion of anterior surface 212. As shown in FIG. 4, vertebral body V3 has been shaped, or modified from its natural state to accommodate the retaining mechanism 260 at area 261 that abuts the anterior surface 212 of vertebral body V3. Note that the anterior surface 212 need not be shaped, however, to accommodate the retaining mechanism 260 at area 261. That is, at area 261, the retaining mechanism 260 may be configured to abut the natural shape of the anterior surface 212 of vertebral body V3.

Further, as shown in FIG. 4, fastener 240 passes through the retaining mechanism and through component 220 so that the fastener 240 can engage the vertebral body V3, as shown. In FIG. 4, the prosthesis 302 is a motion-preserving device.

Fastener 240 has a distal end 244 and a fastener head 242. As shown, fastener 240 is a screw. As shown in FIG. 4, the retaining system 300 is configured so that the fastener 240 can penetrate the vertebral body V3, and more particularly, the system 300 is configured so that the fastener 240 is received from an anterior direction. Further, as shown in FIG. 4, the retaining mechanism 260 further comprises a fastener-receiving hole 269 configured to receive the fastener 240 and to allow the fastener 240 to engage the vertebral body V3. Also, as shown in FIG. 4, the component 220 further comprises a fastener-receiving hole 229 configured to receive the fastener 140 and to allow the fastener 240 to engage the vertebral body V3. Further, as shown in FIG. 4, both fastener-receiving hole 229 and fastener-receiving hole 269 are configured to allow the fastener 240 to engage the vertebral body V3 in a direction toward a substantial center of the vertebral body V3.

Figure 4A:
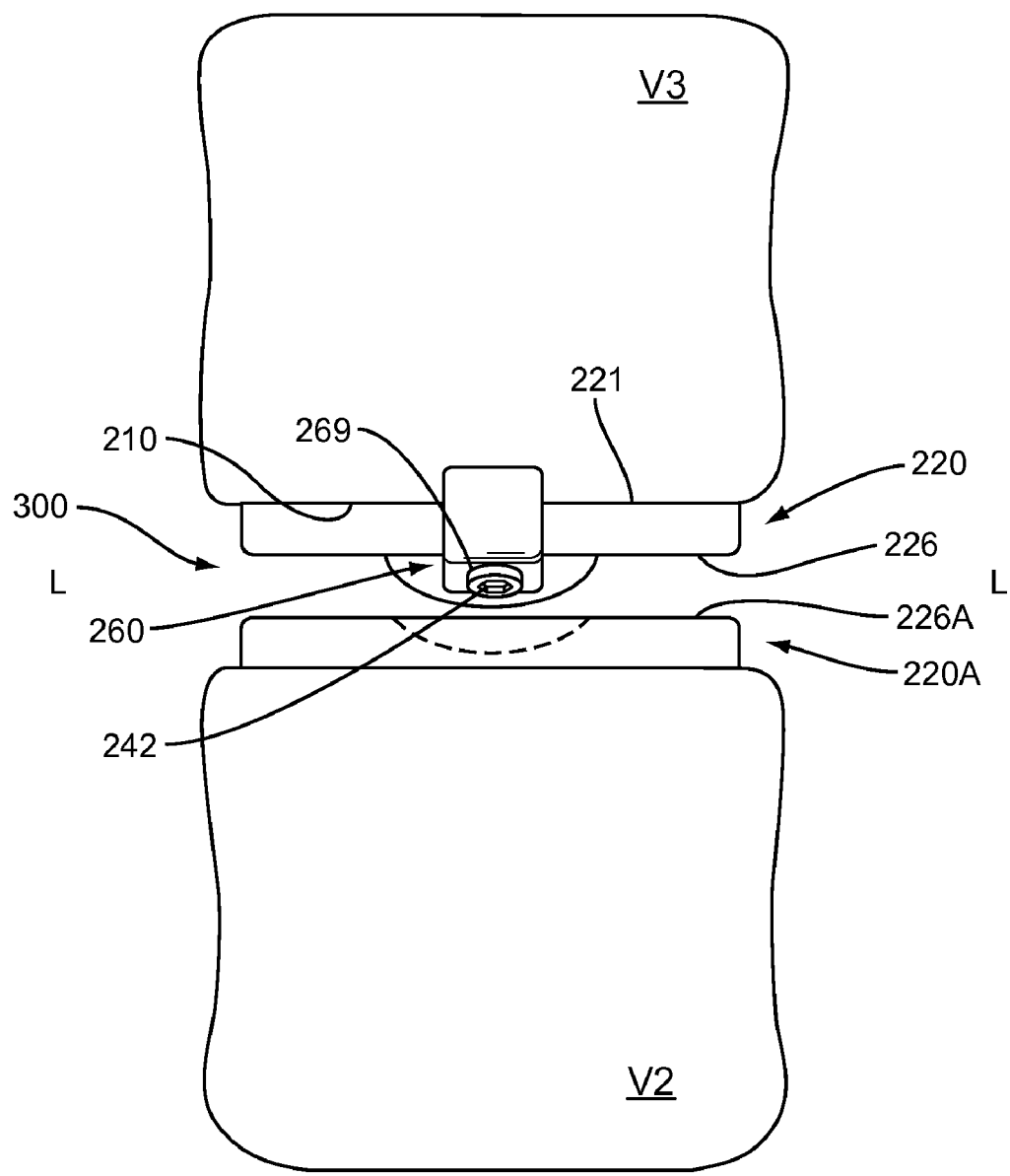
FIG. 4A is a frontal view of the retaining system of FIG. 4.

FIG. 4A shows a frontal view of retaining system 300 of FIG. 4. This view is from the anterior side A of vertebral bodies V3 and V2, where reference marker L represents lateral sides of vertebral bodies V3 and V2. As shown in FIG. 4A, retaining system 300 comprises a single retaining mechanism 260 and a single fastener 240 (of which fastener head 242 is visible). Further, FIG. 4A shows the fastener-receiving hole 269 of retaining mechanism 260, the hole 269 of which is configured to receive fastener 240 and to allow fastener 240 to engage the vertebral body V3. Note that alternate versions of retaining system 300 may have multiple retaining mechanisms (similar to that shown in FIG. 2B) or may have a larger retaining mechanism (similar to that shown in FIG. 2C).

Figure 5:
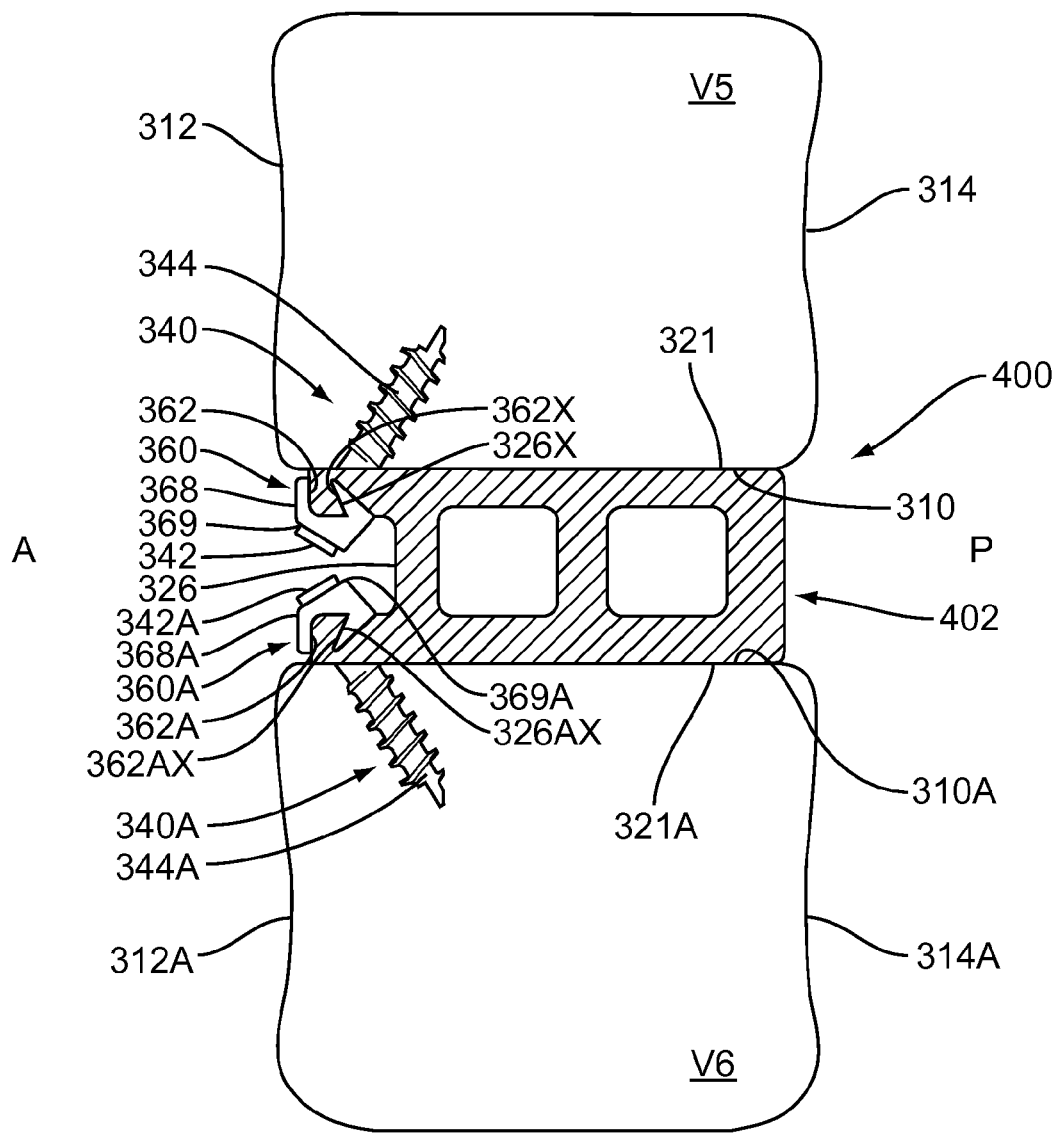
FIG. 5 is a schematic, cross-sectional view of another retaining system in a sagittal plane.

FIG. 5 shows a schematic, cross-sectional view of a retaining system 400 in a sagittal plane, situated substantially in the disc space between vertebral bodies V5 and V6. Reference marker A represents an anterior side of the vertebral bodies V5 and V6, whereas reference marker P represents a posterior side of the vertebral bodies V5 and V6. The system 400 is a retaining system for affixing a prosthesis to a vertebral body. As shown in FIG. 5, the system 400 comprises a prosthesis 402 and two retaining mechanisms 260 and 260A.

With respect to superior retaining mechanism 260, prosthesis 402 comprises a superior inner surface 321 configured to engage at least a portion of an endplate surface 310 of the vertebral body V5, and an outer surface 326 configured to engage the retaining mechanism 360. The outer surface 326 of the prosthesis 402 comprises a first face 326X directed substantially toward the vertebral body V5. The retaining mechanism 360 comprises an inner surface 362 configured to engage the outer surface 326 of the prosthesis 402, and an outer surface 368 configured to receive a fastener 340. The inner surface 362 of the retaining mechanism 360 comprises a second face 362X directed substantially away from the vertebral body.

With respect to inferior retaining mechanism 360A, prosthesis 402 comprises an inferior inner surface 321A configured to engage at least a portion of an endplate surface 310A of the vertebral body V6, and an outer surface 326A configured to engage the retaining mechanism 360A. The outer surface 326 of the prosthesis 402 comprises a first face 326AX directed substantially toward the vertebral body V6. The retaining mechanism 360A comprises an inner surface 362A configured to engage the outer surface 326A of the prosthesis 402, and an outer surface 368A configured to receive a fastener 340A. The inner surface 362A of the retaining mechanism 360A comprises a second face 362AX directed substantially away from the vertebral body V6.

Further, as shown in FIG. 5, fasteners 340 and 340A pass through the retaining mechanisms 360 and 360A, respectively, and through prosthesis 402 so that the fasteners 440 and 440A can engage the vertebral bodies V5 and V6, as shown. In FIG. 5, the prosthesis 402 is a fusion device.

Fastener 340 has a distal end 344 and a fastener head 342. As shown, fastener 340 is a screw. As shown in FIG. 5, the retaining system 400 is configured so that the fastener 340 can penetrate the vertebral body V5, and more particularly, the system 400 is configured so that the fastener 340 is received from an anterior direction. Further, as shown, the retaining mechanism 360 further comprises a fastener-receiving hole 369 configured to receive the fastener 340 and to allow the fastener 340 to engage the vertebral body V5. Also, the prosthesis 402 further comprises a fastener-receiving hole 329 configured to receive the fastener 340 and to allow the fastener 340 to engage the vertebral body V5. Further, as shown in FIG. 5, both fastener-receiving hole 329 and fastener-receiving hole 369 are configured to allow the fastener 340 to engage the vertebral body V5 in a direction toward a substantial center of the vertebral body V5.

Fastener 340A has a distal end 344A and a fastener head 342A. As shown, fastener 340A is a screw. As shown in FIG. 5, the retaining system 400 is configured so that the fastener 340A can penetrate the vertebral body V6, and more particularly, the system 400 is configured so that the fastener 340A is received from an anterior direction. Further, as shown, the retaining mechanism 360A further comprises a fastener-receiving hole 369A configured to receive the fastener 340A and to allow the fastener 340A to engage the vertebral body V6. Also, the prosthesis 402 further comprises a fastener-receiving hole 329A configured to receive the fastener 340A and to allow the fastener 340A to engage the vertebral body V6. Further, as shown in FIG. 5, both fastener-receiving hole 329A and fastener-receiving hole 369A are configured to allow the fastener 340A to engage the vertebral body V6 in a direction toward a substantial center of the vertebral body V6.

Figure 5A:
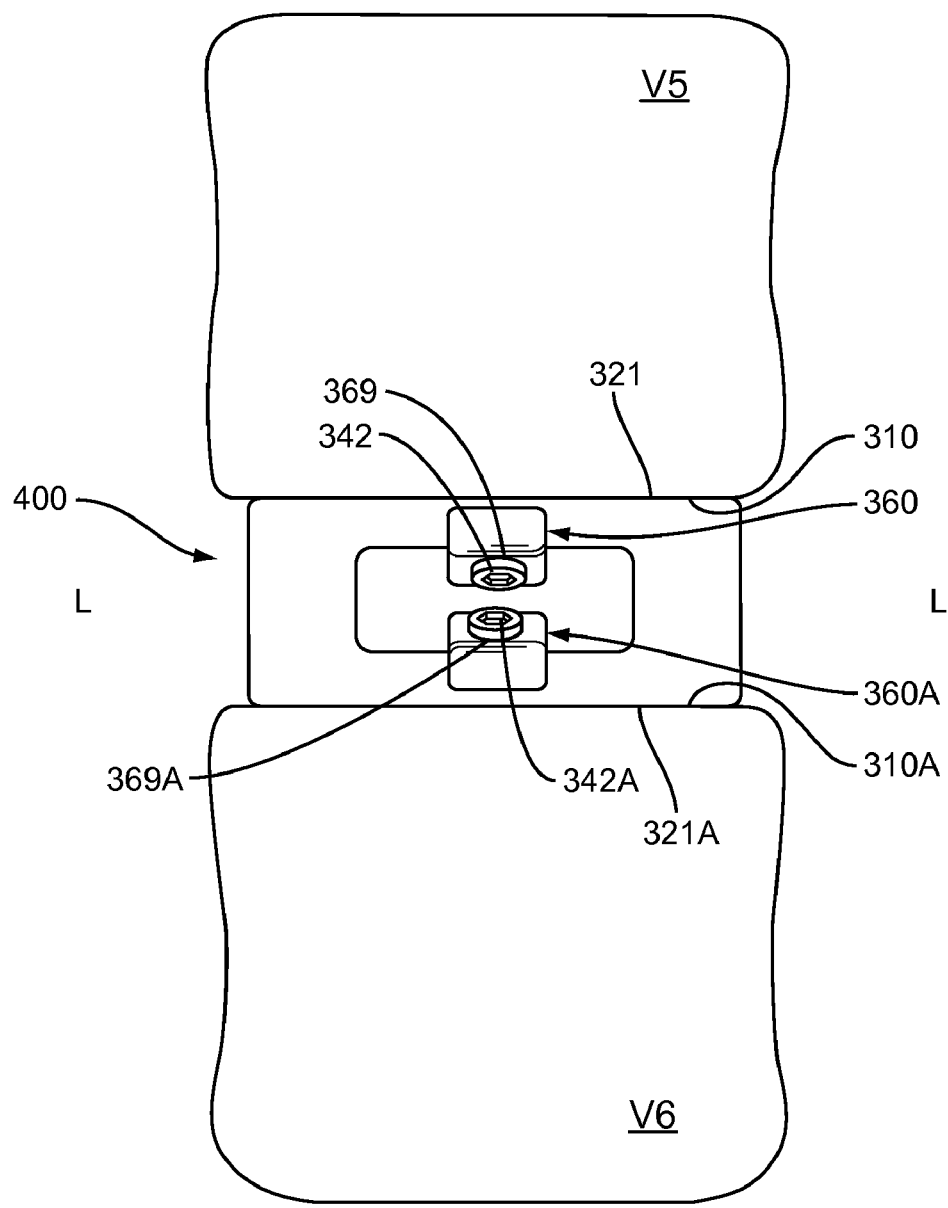
FIG. 5A is a frontal view of the retaining system of FIG. 5.

FIG. 5A shows a frontal view of retaining system 400 of FIG. 5. This view is from the anterior side A of vertebral bodies V5 and V6, where reference marker L represents lateral sides of vertebral bodies V5 and V6. As shown in FIG. 5A, retaining system 400 comprises retaining mechanisms 360 and 360A and fasteners 340 and 340 (of which fastener heads 342 and 342A are visible), respectively. Further, FIG. 5A shows the fastener-receiving holes 369 and 369A of retaining mechanisms 360 and 360A, respectively, the holes 369 and 369A of which are configured to receive fasteners 340 and 340A, respectively, and to allow fasteners 340 and 340A to engage the vertebral bodies V5 and V6. Note that with alternate version of the retaining system 400, the number and/or location and/or shape of the retaining mechanisms may be different than that shown in FIG. 5A.

Any of the components, retaining mechanisms or fasteners described herein may be made of any suitable biocompatible material. Suitable biocompatible materials include, but are not limited to, any of the following or any combination of the following: metals such as Titanium Alloys, commercially available Titanium, stainless steel, cobalt chrome ("CoCr") and shape memory metals, and polymers such as polyetheretherketone ("PEEK"), ultra high molecular weight polyethylene ("UHMWPE") and polyethylene. One embodiment comprises a component made of PEEK, a fastener made of PEEK and a retaining mechanism made of a metal such as stainless steel.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. For example, prostheses 102, 202 and 302 are shown as motion-preserving devices, but can be modified to be fusion devices. Similarly, prosthesis 402 is shown as fusion device, but can be modified to be a motion-preserving device. Also, although only the superior component of prostheses 102, 202, and 302 are shown as having a retaining mechanism, both components may each utilize a retaining mechanism, or merely only the inferior component may utilize a retaining mechanism. Further, although all of the prostheses above are described as being configured to affix to an endplate of a vertebral body from an anterior direction, all of the prostheses above may be configured to affix to a vertebral body from a posterior direction, a lateral direction instead of or as well as from an anterior direction.

Furthermore, as used herein, the terms components and modules may be interchanged. It is understood that all spatial references, such as "superior," "inferior," "inner," and "outer" are for illustrative purposes only and can be varied within the scope of the disclosure.

The invention claimed is:

1. A retaining system for affixing a component to a vertebral body, the system comprising:
   a component comprising:
      an inner surface configured to engage at least a portion of an endplate surface of the vertebral body; and
      an outer surface extending from the anterior side of the vertebral body to the posterior side of the vertebral body and parallel to the to the endplate surface configured to engage a retaining mechanism, the outer surface of the component comprising a first face directed substantially toward the vertebral body; and
   a retaining mechanism comprising:
      an inner surface configured to engage the outer surface of the component, the inner surface of the retaining mechanism comprising a second face directed substantially away from the vertebral body; and
      an outer surface configured to receive a fastener.

2. The system of claim 1, wherein the inner surface of the retaining mechanism comprises a recessed area.

3. The system of claim 1, wherein the inner surface of the retaining mechanism is not curved in the sagittal plane.

4. The system of claim 1 configured so that the fastener can penetrate the vertebral body.

5. The system of claim 1 configured so that the fastener is received from an anterior direction.

6. The system of claim 1, wherein the component is or is part of a fusion device.

7. The system of claim 1, wherein the system is or is part of a motion-preserving device.

8. The system of claim 1, wherein the retaining mechanism further comprises a fastener-receiving hole configured to receive the fastener and to allow the fastener to engage the vertebral body.

9. The system of claim 1, wherein the component further comprises a fastener-receiving hole configured to receive the fastener and to allow the fastener to engage the vertebral body.

10. The system of claim 9, wherein the fastener-receiving hole is configured to allow the fastener to engage the vertebral body in a direction toward a substantial center of the vertebral body.

11. The system of claim 1, wherein the inner surface of the retaining mechanism is further configured to engage at least a portion of a vertical surface of the vertebral body.

12. A retaining system for affixing a component to a vertebral body, the system comprising:
   a component comprising:
      an inner surface configured to engage at least a portion of an endplate surface of the vertebral body; and
      an outer surface extending from the anterior side of the vertebral body to the posterior side of the vertebral body and parallel to the to the endplate surface configured to engage a retaining mechanism, the outer surface of the component comprising a first face directed substantially toward the vertebral body; and
   a retaining mechanism comprising:
      an inner surface configured to engage the outer surface of the component and configured to engage at least a portion of a vertical surface of the vertebral body, the inner surface of the retaining mechanism comprising a second face directed substantially away from the vertebral body; and
      an outer surface configured to receive a fastener.

13. The system of claim 12, wherein the inner surface of the retaining mechanism comprises a recessed area.

14. The system of claim 13, wherein the inner surface of the retaining mechanism is not curved in the sagittal plane.

15. The system of claim 12 configured so that the fastener can penetrate the vertebral body.

16. The system of claim 12, wherein the vertical surface of the vertebral body is an anterior surface of the vertebral body, the system configured so that the fastener is received from an anterior direction.

17. The system of claim 12, wherein the system is or is part of a motion-preserving device.

18. The system of claim 12, wherein the retaining mechanism further comprises a fastener-receiving hole configured to receive the fastener and to allow the fastener to engage the vertebral body.

19. The system of claim 12, wherein: the component further comprises a fastener-receiving hole configured to receive the fastener and to allow the fastener to engage the vertebral body; and the fastener-receiving hole is configured to allow the fastener to engage the vertebral body in a direction toward a substantial center of the vertebral body.

20. A retaining system for affixing a component to a vertebral body, the system comprising:

a component comprising:
- an inner surface configured to engage at least a portion of an endplate surface of the vertebral body;
- an outer surface extending from the anterior side of the vertebral body to the posterior side of the vertebral body and parallel to the to the endplate surface configured to engage a retaining mechanism, the outer surface of the component comprising a first face directed substantially toward the vertebral body; and
- a fastener-receiving hole to allow a fastener to engage the vertebral body; and a retaining mechanism comprising:
- an inner surface configured to engage the outer surface of the component, the inner surface of the retaining mechanism comprising a second face directed substantially away from the vertebral body; and
- a fastener-receiving hole to allow the fastener to engage the vertebral body.

* * * * *